US012664646B2

(12) United States Patent
Balch et al.

(10) Patent No.: US 12,664,646 B2
(45) Date of Patent: *Jun. 23, 2026

(54) IMAGE-BASED CIRCULAR PLOT RECOGNITION AND INTERPRETATION

(71) Applicant: NANT HOLDINGS IP, LLC, El Segundo, CA (US)

(72) Inventors: Carla W. Balch, Memphis, TN (US); Nicholas J. Witchey, Laguna Hills, CA (US)

(73) Assignee: Nant Holdings IP, LLC, El Segundo, CA (US)

( * ) Notice: Subject to any disclaimer, the term of this patent is extended or adjusted under 35 U.S.C. 154(b) by 253 days.

This patent is subject to a terminal disclaimer.

(21) Appl. No.: 18/315,395

(22) Filed: May 10, 2023

(65) Prior Publication Data

US 2023/0281811 A1     Sep. 7, 2023

Related U.S. Application Data

(63) Continuation of application No. 16/664,643, filed on Oct. 25, 2019, now Pat. No. 11,688,060, which is a (Continued)

(51) Int. Cl.
| | |
|---|---|
| *G06T 7/00* | (2017.01) |
| *G06T 3/02* | (2024.01) |
| *G06T 7/11* | (2017.01) |
| *G06T 7/13* | (2017.01) |
| *G06V 10/10* | (2022.01) |

(Continued)

(52) U.S. Cl.
CPC .............. *G06T 7/0012* (2013.01); *G06T 3/02* (2024.01); *G06T 7/11* (2017.01); *G06T 7/13* (2017.01); *G06V 10/17* (2022.01); *G06V*

*30/422* (2022.01); *G16B 20/00* (2019.02); *G06T 2207/10056* (2013.01); *G06T 2207/30072* (2013.01);

(Continued)

(58) Field of Classification Search
None
See application file for complete search history.

(56) References Cited

U.S. PATENT DOCUMENTS

| | | | |
|---|---|---|---|
| 4,876,728 A | 10/1989 | Roth | |
| 6,711,293 B1 | 3/2004 | Lowe | |

(Continued)

FOREIGN PATENT DOCUMENTS

| | | |
|---|---|---|
| CN | 102306383 | 1/2012 |
| WO | 2015056210 | 4/2015 |

OTHER PUBLICATIONS

Krzywinski et al., "Circos: An information aesthetic for comparative genomics", Published in Advance Jun. 18, 2009, doi:10.1101/gr.092759.109.

*Primary Examiner* — Nancy Bitar
(74) *Attorney, Agent, or Firm* — STETINA GARRED BRUCKER & NEWBOLES

(57)                    ABSTRACT

A device includes software instructions for a circular plot analysis agent and at least one circular plot definition. The circular plot analysis agent obtains a digital image of a circular plot, detects a perimeter of the circular plot within the digital image, detects a plurality of edges within the perimeter, identifies a set of endpoints on the perimeter as a function of the plurality of edges, generates a plot descriptor from the set of endpoints, and initiates a transaction with a second device as a function of the plot descriptor.

20 Claims, 8 Drawing Sheets

Related U.S. Application Data continuation of application No. 15/785,008, filed on Oct. 16, 2017, now Pat. No. 10,460,446.

(51) Int. Cl.

| | | |
|---|---|---|
| *G06V 30/422* | (2022.01) | |
| *G16B 20/00* | (2019.01) | |
| *G16B 30/00* | (2019.01) | |
| *G16H 50/00* | (2018.01) | |
| *G16B 45/00* | (2019.01) | |

(52) U.S. Cl.
CPC .............. *G16B 30/00* (2019.02); *G16B 45/00* (2019.02); *G16H 50/00* (2018.01)

(56)                    References Cited

U.S. PATENT DOCUMENTS

| | | | |
|---|---|---|---|
| 7,016,532 B2 | 3/2006 | Boncyk et al. | |
| 7,477,780 B2 | 1/2009 | Boncyk et al. | |
| 7,680,324 B2 | 3/2010 | Boncyk et al. | |
| 8,396,327 B2 | 3/2013 | Spyridonos et al. | |
| 8,583,209 B2 | 11/2013 | Maier | |
| 8,866,924 B2 | 10/2014 | Tang et al. | |
| 9,412,176 B2 | 8/2016 | Song et al. | |
| 9,646,134 B2 | 5/2017 | Sanborn et al. | |
| 9,652,587 B2 | 5/2017 | Sanborn et al. | |
| 9,665,606 B2 | 5/2017 | Song et al. | |
| 11,101,032 B2 * | 8/2021 | Kohle | G06V 10/454 |
| 11,688,060 B2 * | 6/2023 | Balch | G06V 30/422 |
| | | | 382/129 |
| 2003/0013951 A1 * | 1/2003 | Stefanescu | G06F 16/5838 |
| | | | 600/407 |
| 2009/0019088 A1 | 1/2009 | Fernandez | |
| 2010/0152594 A1 | 6/2010 | Bhat et al. | |
| 2014/0115515 A1 * | 4/2014 | Adams | G16B 20/20 |
| | | | 715/771 |
| 2015/0031641 A1 | 1/2015 | Levine et al. | |
| 2015/0332283 A1 | 11/2015 | Witchey | |
| 2015/0363663 A1 | 12/2015 | Tombari et al. | |
| 2016/0072800 A1 | 3/2016 | Soon-Shiong et al. | |
| 2016/0334385 A1 | 11/2016 | Prais et al. | |
| 2017/0351708 A1 | 12/2017 | Lahmann et al. | |
| 2018/0089840 A1 * | 3/2018 | Yan | G06T 7/0014 |
| 2018/0314795 A1 * | 11/2018 | Cheung | G06F 40/169 |

* cited by examiner

OBTAIN DIGITAL IMAGE OF CIRCULAR PLOT — S291

DETECT PERIMETER OF CIRCULAR PLOT — S292

TRANSFORM PERIMETER — S293

DETECT EDGES WITHIN PERIMETER — S294

IDENTIFY END POINTS — S295

GENERATE PLOT DESCRIPTOR — S296

INITIATE TRANSACTION — S297

Captured Image
of Circular Plot
310

Affine Transform
320

Transformed
Circular Plot
330

IMAGE-BASED CIRCULAR PLOT RECOGNITION AND INTERPRETATION

CROSS-REFERENCE TO RELATED APPLICATIONS

This application is a continuation of U.S. patent application Ser. No. 16/664,643, filed on Oct. 25, 2019, now U.S. Pat. No. 11,688,060, issued Jun. 27, 2023, which is a continuation of U.S. patent application Ser. No. 15/785,008, filed on Oct. 16, 2017, now U.S. Pat. No. 10,460,446 issued Oct. 29, 2019, and entitled IMAGE-BASED CIRCULAR PLOT RECOGNITION AND INTERPRETATION, the disclosures of which are hereby incorporated by reference in their entirety.

STATEMENT RE: FEDERALLY SPONSORED RESEARCH/DEVELOPMENT

Not Applicable

BACKGROUND

1. Technical Field

The present inventive subject matter relates to image recognition technologies associated with circular plots, including genomic circular plots.

2. Background

The background description includes information that may be useful in understanding the present inventive subject matter. It is not an admission that any of the information provided herein is prior art or applicant admitted prior art, or relevant to the presently claimed inventive subject matter, or that any publication specifically or implicitly referenced is prior art or applicant admitted prior art.

Circular plots have grown in popularity within the scientific communities. Circular plots are able to condense an extremely large amount of information into an ink efficient and space efficient visual package. There are numerous circular plotting packages available, including the Circos® package that pioneered the effort, which can be found at URL circos.ca (Martin I Krzywinski, Jacqueline E Schein, Inanc Birol, Joseph Connors, Randy Gascoyne, Doug Horsman, Steven J Jones, and Marco A Marra, Genome Res. Published in Advance Jun. 18, 2009, doi:10.1101/gr.092759.109).

Circular plots can vary widely depending on the information they are required to present. Examples of fairly simple circular plots can be found in U.S. Patent Application Pub. No. 2015/0031641 to Ross L. Levine et al., published Jan. 29, 2015, entitled "Methods and Compositions for the Diagnosis, Prognosis and Treatment of Acute Myeloid Leukemia" ("the '641 publication"). See, for example, FIGS. 1a-1c, 6a-6n, 7a-7c, and 8a of the '641 publication. As described in paragraph [0032] of the '641 publication, FIG. 1 is a Circos® diagram depicting relative frequency and pairwise co-occurrence of mutations in de novo AML patients enrolled in the ECOG protocol E1900 (Panel A), in which the arc length corresponds to the frequency mutations in the first gene and the ribbon width corresponds to the percentage of patients that also have a mutation in the second gene. Further, circular plots can also become quite complex representing dense, rich information. An example of a relatively complex circular plot can be found in U.S.

Patent Application Pub. No. 2014/0115515 to Julie Adams et al., published Apr. 24, 2014, entitled "Genome Explorer System to Process and Present Nucleotide Variations in Genome Sequence Data" ("the '515 publication"). See, for example, FIG. 3A of the '515 publication. As described in paragraph [0064] of the '515 publication, FIG. 3A is an overview display of the entire genome sequence of a patient sample in the form of a circular or Circos®-style plot, in which the frequency of structural variations at locations across the chromosome map are shown and curved lines in the middle show apparent interchromosomal junctions.

Circular plots similar to the one depicted in FIG. 3A of the '515 publication are typically used to present detailed information to one or more stakeholders. Typically, such plots are incorporated into scientific presentations. However, the circular plots can also be used by one or more healthcare providers. For example, a doctor might request that a cancer patient obtain a GPS Cancer™ test, such as those offered by NantHealth, Inc. (see URL www.gpscancer.com). One possible result from the test could include a detailed circular plot showing a condensed representation of a whole genome sequence of the patient's tumor.

Interestingly, complex genomic circular plots have disadvantages in view of their ability to present a vast amount of information in compact form. On one hand, a stakeholder is able to assess quickly an overview of a patient's genomic status based on the observed information. However, on the other hand, the stakeholder would have to pour over the circular plot to find detailed information, which is time consuming. Further, the stakeholder lacks the ability to compare one circular plot to other similar circular plots in order to make detailed comparisons relating to treatment, diagnosis, or prognosis.

It is possible to leverage existing image recognition technologies that could "recognize" an image of a circular plot among many plots. For example, a circular plot could be analyzed by an implementation of a scale invariant feature transform (SIFT) algorithm as described in U.S. Pat. No. 6,711,293 to Lowe titled "Method and Apparatus for Identifying Scale Invariant Features in an Image and Use of Same for Locating an Object in an Image," filed on Mar. 6, 2000, the content and substance of which is incorporated herein by reference. The algorithm yields one or more SIFT descriptors, which can then be used as an index to look up information about the recognized plot. Other examples of descriptors include those described in U.S. Pat. No. 8,866, 924 to Tang et al. titled "Local Image Feature Descriptors According to Circular Distribution Information," filed Oct. 28, 2011, the content and substance of which is incorporated herein by reference, and U.S. Pat. No. 9,412,176 to Song et al. titled "Image-based Feature Detection using Edge Vectors," filed May 6, 2015, the content and substance of which is incorporated herein by reference.

Searching based on salient parameters is described in U.S. Pat. No. 7,016,532 to Boncyk et al. titled "Image Capture and Identification Systems and Process," filed on Nov. 5, 2001, the content and substance of which is incorporated herein by reference; U.S. Pat. No. 7,477,780 to Boncyk et al. also titled "Image Capture and Identification Systems and Process," filed internationally on Nov. 5, 2002, the content and substance of which is incorporated herein by reference; and U.S. Pat. No. 7,680,324 to Boncyk et al. titled "Use of Image-Derived Information as Search Criteria for Internet and Other Search Engines," filed on Aug. 15, 2005, the content and substance of which is incorporated herein by reference. While these computer-based techniques provide utility with respect to returning indexed information about an a priori known image or an a priori known object in an image, they would fail or lack efficiency with respect to providing an actual interpretation of the information contained in a complex genomic plot that is newly generated or not yet known.

At the other end of the spectrum, techniques such as those employed for reading bar codes yield exact interpretations. However, especially in the case of complex genomics circular plots, it is not yet possible for a computing device to provide an exact interpretation of the data represented in the circular plot for multiple reasons. One example difficulty is that the circular plots can include a fine level of detail that cannot necessarily be captured by an imaging device. The loss of fidelity in the captured image results in loss of information during analysis. Another example difficulty is that there are no standard definitions for genomic circular plots by which such plots can be interpreted. Thus, it is not necessarily possible for a device to a priori know what type of plot it is viewing in order to generate a meaningful interpretation.

Even beyond the difficulties associated with a computing device interpreting the information in a genomic circular plot, stakeholders such as healthcare providers would benefit from initiating transactions from captured images of such circular plots. For example, a doctor would benefit from quickly capturing an image of a patient's genomic circular plot and then initiating a prescription or matching the patient to clinical trials, just to name a few benefits. Thus, there remains a considerable need for technologies to convert observed circular plots into meaningful actions.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

BRIEF SUMMARY

The inventive subject matter provides apparatus, systems and methods in which one or more computing devices are configured to initiate transactions based on a digitally observed circular plot. One aspect of the inventive subject matter includes a computing device having a computer readable memory and at least one processor. The computing device may be a cell phone or computer server for example. The memory may store software instructions that encode a machine executable circular plot analysis agent. Further, in some embodiments, the memory stores one or more circular plot definitions that describe potentially observable circular plot types. The processor in the device is configured to operate as the circular plot analysis agent upon execution of the corresponding software instructions. The circular plot analysis agent includes multiple functionalities that focus on initiating one or more transactions based on digitally observing a circular plot, a whole genome sequence plot of a tumor for example. The agent obtains a digital image of a circular plot, possibly via an optical sensor (e.g., camera, CMOS, CCD, etc.). In some embodiments the digital image does not properly align with the original plot such that the image of the circular plot is skewed. In such embodiments, the agent is able to digitally transform (e.g., affine transform, stretch, rotate, translate, etc.) the image of the circular plot to ensure the image of the circular plot has a circular form for further processing.

The agent continues by detecting one or more perimeters of the circular plot in the digital image. There could be more than one perimeter, possibly associated with multiple tracks of information. The agent also detects a plurality of edges within a perimeter of the circular plot. Edge detection techniques can be based on Canny edges, edge descriptors, edge constellation descriptors or other types of edge detection algorithms. The agent leverages the edges to map internal chords, if any, of the circular plot to endpoints located on the perimeter of the plot. Thus, the agent identifies a set of endpoints distributed around the perimeter as a function of the plurality of edges. The agent then generates one or more plot descriptors from the set of endpoints and/or the plurality of edges. For example, a plot descriptor could comprise a histogram of endpoint clusters where each bin in the histogram represents a segment of a track around the perimeter of the plot. With the plot descriptors in hand, the agent is able to initiate one or more electronic transactions by using the descriptors as a command code, an index into a look-up table, a query to a database or other construct.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
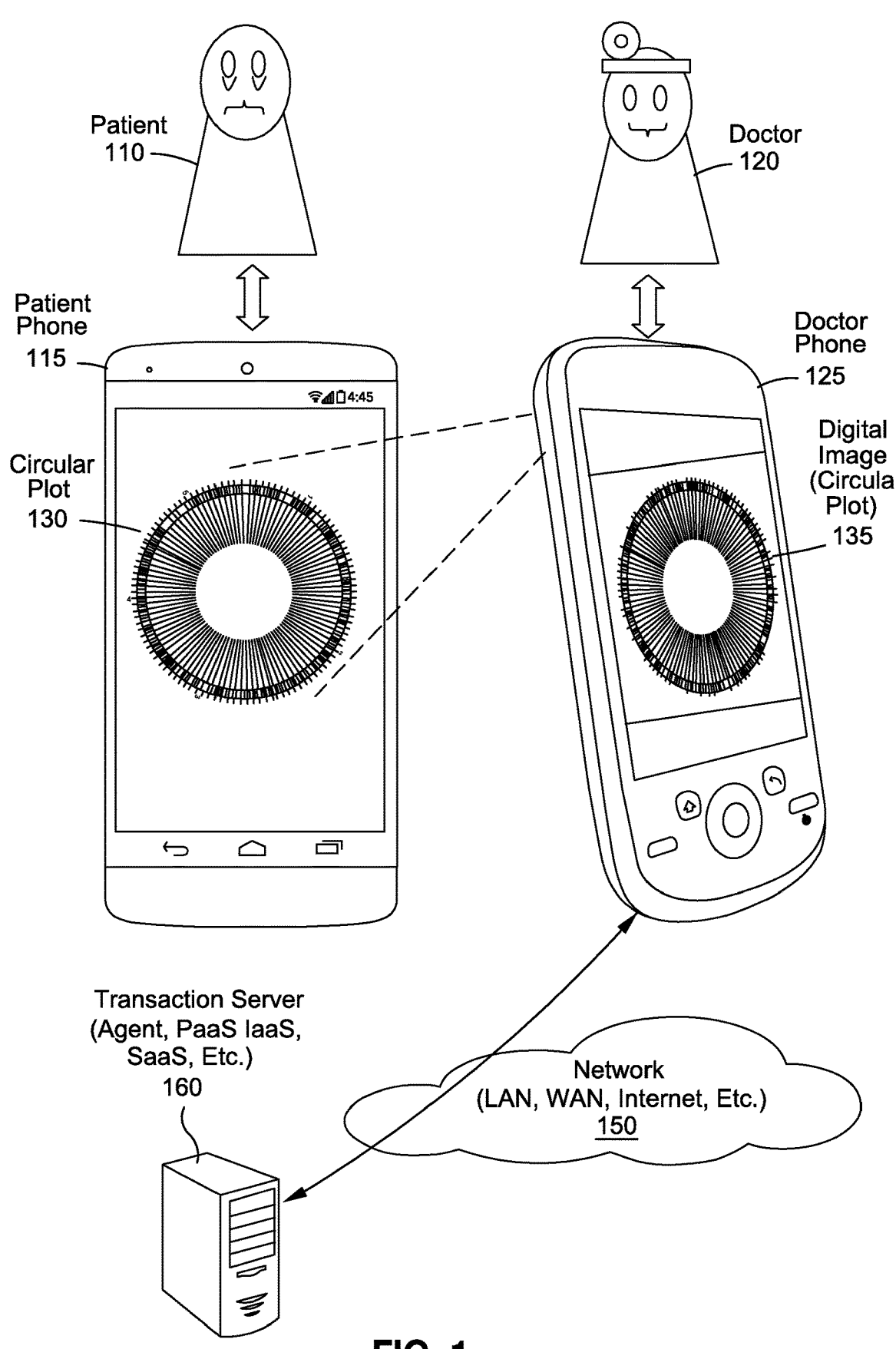
FIG. 1 presents an overview of a doctor-patient interaction that leverages recognition of a circular plot.

The detailed description set forth below in connection with the appended drawings is intended as a description of certain embodiments of an image-based circular plot recognition and interpretation system and is not intended to represent the only forms that may be developed or utilized. The description sets forth the various structure and/or functions in connection with the illustrated embodiments, but it is to be understood, however, that the same or equivalent structure and/or functions may be accomplished by different embodiments that are also intended to be encompassed within the scope of the present disclosure. It is further understood that the use of relational terms such as first and second, and the like are used solely to distinguish one entity from another without necessarily requiring or implying any actual such relationship or order between such entities.

It should be noted that any language directed to a computer should be read to include any suitable combination of computing devices, including servers, interfaces, systems, databases, agents, peers, engines, controllers, modules, or other types of computing devices operating individually or collectively. One should appreciate the computing devices comprise at least one processor, possibly having one or more cores, configured to execute software instructions stored on a tangible, non-transitory computer readable storage medium (e.g., hard drive, FPGA, PLA, solid state drive, RAM, flash, ROM, etc.). The software instructions configure or program the computing device to provide the roles, responsibilities, facilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In some embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

As used in the description herein and throughout the claims that follow, when a system, engine, server, device, module, or other computing element is described as configured to perform or execute functions on data in a memory, the meaning of "configured to" or "programmed to" is defined as one or more processors or cores of the computing element being programmed by a set of software instructions stored in the memory of the computing element to execute the set of functions on target data or data objects stored in the memory.

One should appreciate that the disclosed techniques provide many advantageous technical effects including causing a computing device to take electronic action based on digitally observing a circular plot. The device converts digital image data of one or more circular plots into plot descriptors, which carry some meaning from the plots. Further, the plot descriptors can then be used as a code to initiate one or more electronic transactions (e.g., query a database, initiate a prescription, update a healthcare records, initiate a machine learning function, etc.).

The focus of the disclosed inventive subject matter is to enable construction or configuration of a computing device to operate on vast quantities of digital data, dense image data of circular plots for example, beyond the capabilities of a human. Although the digital data represents whole genome sequence data, for example, it should be appreciated that the digital data is a representation of one or more digital models of "omics" information not a genome itself for example. By instantiation of such digital models in the memory of the computing devices, the computing devices are able to manage the digital data or models in a manner that could provide utility to a user of the computing device that the user would lack without such a tool.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the inventive subject matter are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the inventive subject matter are approximations, the numerical values set forth in the specific examples are reported as precisely as practicable. The numerical values presented in some embodiments of the inventive subject matter may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the inventive subject matter and does not pose a limitation on the scope of the inventive subject matter otherwise claimed. No language in the specification should be construed as indicating any non-claimed element essential to the practice of the inventive subject matter.

Groupings of alternative elements or embodiments of the inventive subject matter disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

FIG. 1 presents an overview of a doctor-patient interaction that leverages recognition of a circular plot 130. In the example of FIG. 1, a patient 110 possesses a circular plot 130 as an image file viewable on the screen of patient phone 115 or other device (e.g. cell phone, smart phone, personal data assistant, tablet, phablet, computer, medical device, robot, vehicle). In some scenarios, circular plot 130 might be presented in a printed form, possibly as part of a paper-based report. The circular plot 130 may depict any type of data, especially medical data, and most especially genomic medical data such as a whole genome sequence, including ploidy, copy number, repeat copy number, inversion, insertion of viral genes, somatic mutations, germline mutations, structural rearrangements, chromosomal rearrangements, transposition, loss of heterozygosity, allele fraction, etc. For example, the information presented in circular plot 130 could describe differences between a patient's normal or healthy tissue and the patient's tumor or diseased tissue. Such differences can be readily measured based on whole genome sequences leveraging the BAMBAM techniques described in U.S. Pat. No. 9,652,587, filed May 25, 2011, and U.S. Pat. No. 9,646,134, filed Nov. 18, 2011, both to Sanborn et al. titled "BAMBAM: Parallel comparative Analysis of High-Throughput Sequencing Data," the content and substance of both which is incorporated herein by reference. The circular plot 130 may include a plurality of chords connecting endpoints on a perimeter track, where the endpoints may represent base pairs, codons, exons, introns, genes, mutations, single nucleotide polymorphisms, transcriptions, insertions, deletions, etc. The image file may, for example, be stored in the memory of the patient phone 115. The image file can be stored in the memory of the patient phone 115, by way of example when the patient 110 received medical test results including the circular plot 130 from a third party. As another example, the image file may be accessible by the patient 110 (e.g. requiring patient login information) at a remote server via a secure connection and the image data may be downloaded for display on the patient phone 115. In addition, the patient 110 could also securely access image data by logging onto a secure website using a browser installed on the phone 115 or other device and thus only temporarily view the image on screen. Alternatively, the circular plot 130 may not be in the form of an image file at all and could be on a printed piece of paper or other medium that the patient 110 carries with him, e.g. a printed genomics card. In each case, the patient 110 would be able to display or show the circular plot 130 to his doctor 120 or healthcare provider. As discussed herein, it is contemplated that the doctor 120 identified herein could be a medical doctor, researcher or other individual providing healthcare services or other clinical services as is customarily or legally permitted.

As explained above, the doctor 120 may, based on her understanding of the type of circular plot 130 and the medical field, interpret some aspects of the circular plot 130 by visual inspection of the plot. For example, the doctor 120 may notice a clustering of chords between certain medically significant positions on a perimeter of the circular plot 130 and be able to make some preliminary conclusions or inferences about the medical condition of the patient 110. On the other hand, it may be difficult for the doctor 120 to glean detailed information by only viewing the circular plot 130 without additional aids, especially comparative information in relation to other circular plots of other patients (or of the same patient 110 related to different aspects of his condition, earlier tests, etc.) which may not be readily available for side-by-side viewing. Therefore, in accordance with the innovations described herein, the doctor may secure a digital image 135 of the circular plot 130, e.g. using her phone 125 or other device. Using a circular plot analysis agent 120 described below (see FIG. 2A), the doctor's phone 125 or other device may then perform a series of operations to generate a plot descriptor 240 of the circular plot 130 and initiate a transaction using the plot descriptor 240, for example, by accessing a transaction server 160 or other device (e.g. cell phone, electronic healthcare card, smart watch, fitness band, vehicle) with the plot descriptor 240 via a network 150. The transaction may be a look-up, query, etc. to compare the plot descriptor 240 with those of other circular plots stored in a database. The resulting output may contain detailed information about the circular plot 130 of the patient 110, comparison information between the circular plot 130 of the patient 110 and other circular plots, presumed or suggested diagnoses, prescriptions, likely clinical outcomes, etc. Such a transaction may assist the doctor 120 in counseling and treating the patient 110.

Figure 2A:
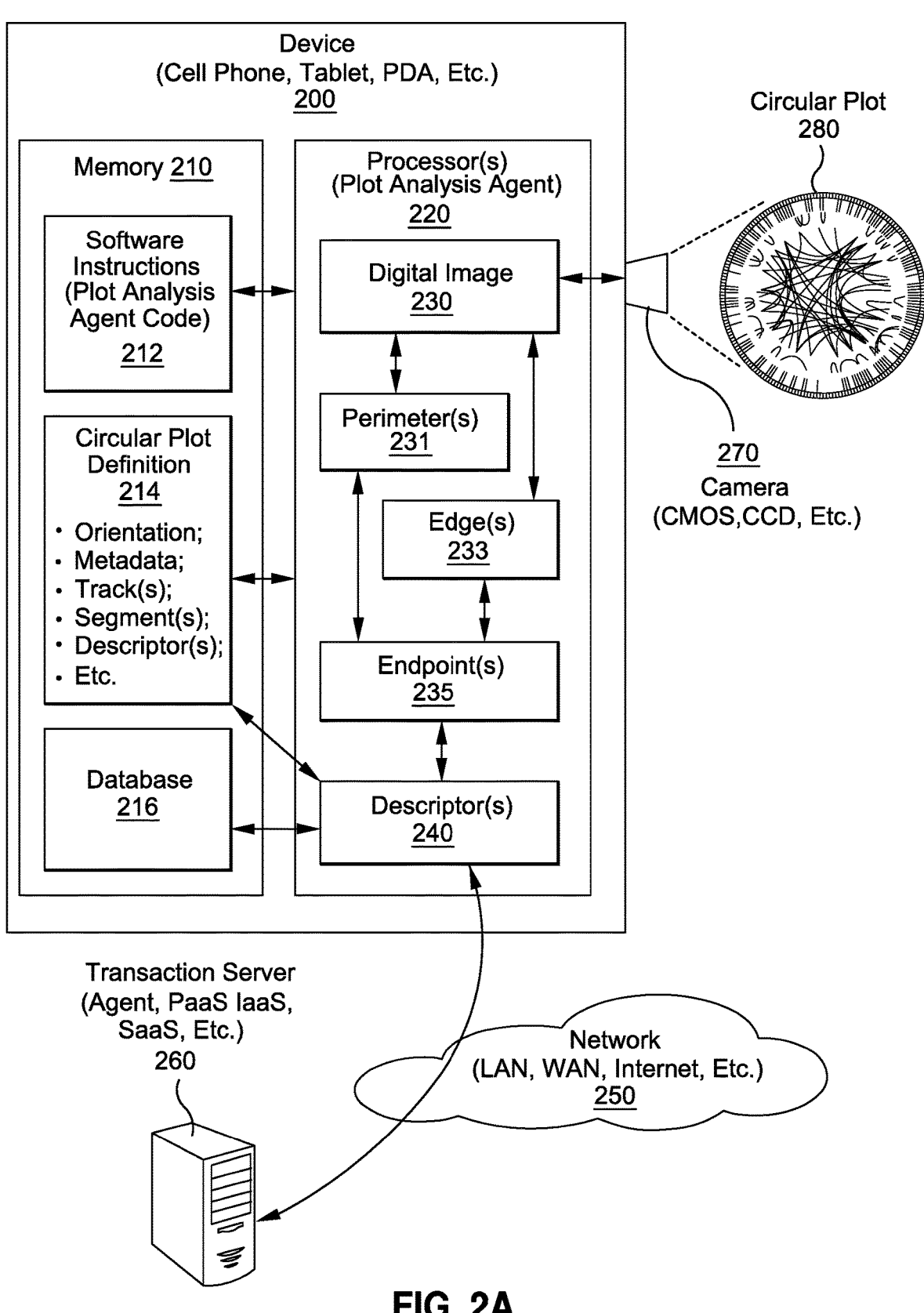
FIG. 2A presents a schematic of an ecosystem with a circular plot recognition device capable of mapping recognized circular plots to one or more transactions.
Figure 2B:
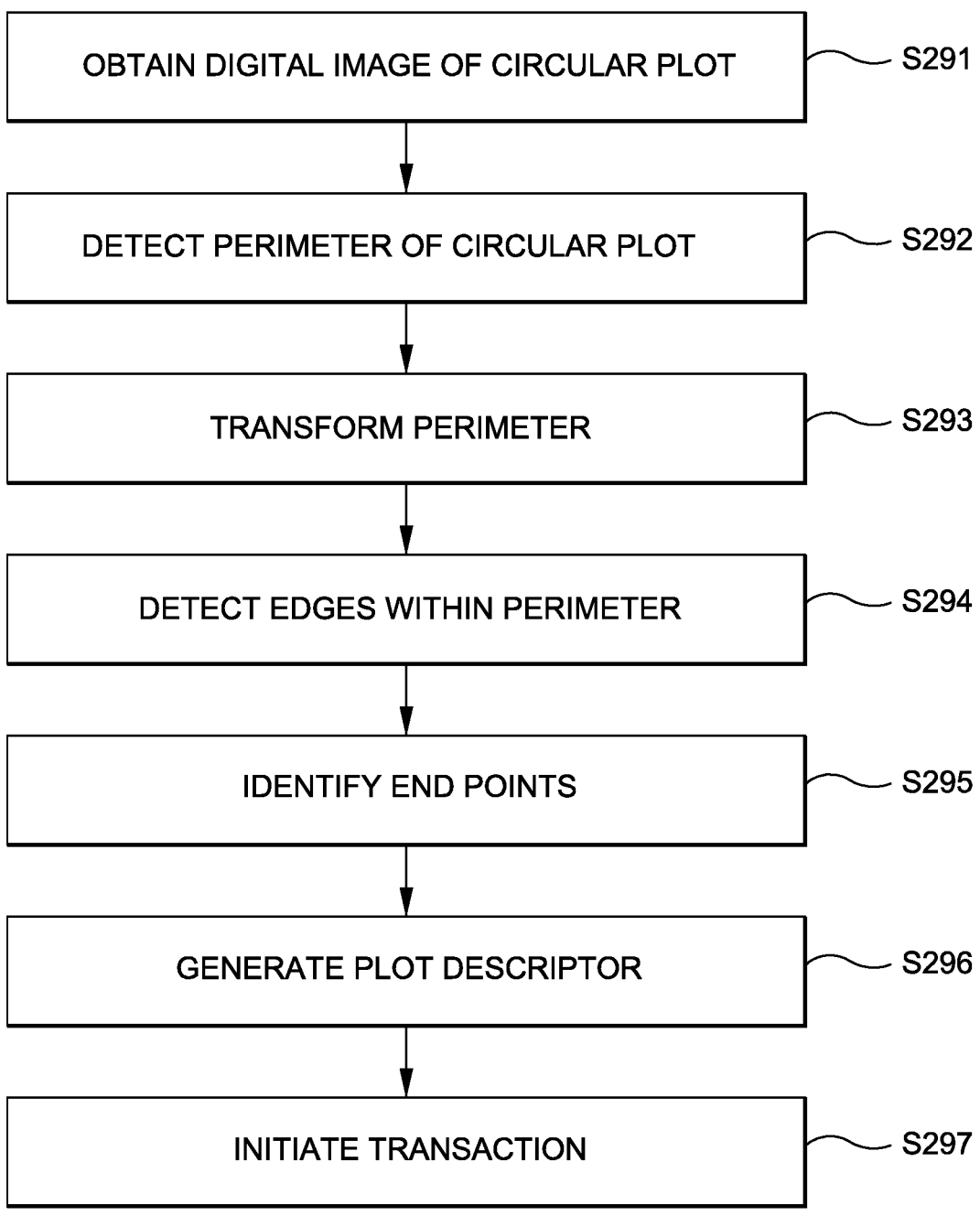
FIG. 2B presents an operational flow in relation to the circular plot recognition device.

FIG. 2A presents a more detailed schematic of an ecosystem with a circular plot recognition device 200 capable of mapping recognized circular plots to one or more transactions. FIG. 2B presents an operational flow in relation to the circular plot recognition device 200. The circular plot recognition device 200 includes a memory 210 and a processor 220 and may be, for example, the doctor's phone 125 of FIG. 1. The device 200 interfaces with a camera 270, which may be built in (e.g. in the case of a smartphone like the doctor's phone 125 of FIG. 1) or otherwise accessible by the device 200 (e.g. in the case of a webcam). Alternatively, the camera 270 may be entirely separate and not accessible by the device 200, with the device 200 simply receiving image data captured by the camera 270 via removable media or a wired or wireless connection and storing it in memory according to one or more image formats (e.g., as jpg, png, bmp, etc.).

Referring the FIGS. 2A and 2B, the processor 220 executes software instructions stored in the memory 210 to function as a circular plot analysis agent that obtains a digital image 230 of a circular plot 280, e.g. the patient's circular plot (see for example 130 of FIG. 1) (S291), detects a perimeter 231 of the circular plot 280 within the digital image 230 (S292), transforms the perimeter 231 as necessary or desired (S293), detects a plurality of edges 233 within the perimeter 231 (S294), identifies a set of endpoints 235 on the perimeter 231 as a function of the plurality of edges 233 (S295), generates at least one plot descriptor 240 from the set of endpoints 235 and/or the plurality of edges 233 (S296), and initiates a transaction as a function of the at least one plot descriptor 240 (S297). The circular plot analysis agent 220 may generate one or more plot descriptor(s) 240 with reference to a circular plot definition 214 stored in the memory 210. As noted above, there are no standard definitions for genomic or other circular plots by which such plots can be interpreted a priori. To this end, the circular plot definition 214 may define, for example, an orientation of the circular plot 280 (e.g. which way is up), metadata associated with the plot (e.g. plot type ID, creator, owner, version number), the number, location(s), and type(s) of circular tracks of the circular plot 280 (e.g. chord connection tracks and other types of tracks having histograms, bar graphs, scales, ranges, etc.), the number, location(s), and/or size(s) of segments along each track, chord and/or endpoint definitions (e.g. placement, size, thickness, color, source/destination), and/or one or more plot descriptor templates for generating the plot descriptor 240. The circular plot definition 214 may further include contextual definitions, including the meaning of each track, segment, etc., such as chromosome labels for each section of a track. Locations of tracks, segments, etc. may be defined relative to the center of the circular plot 280, the perimeter 231, an orientation marker, etc. The circular plot definition 214 may be used by the circular plot analysis agent to generate the plot descriptor 240 as well as at earlier stages of analyzing the circular plot 280, e.g. detecting the perimeter 231, identifying the endpoints 235, etc., as will be described in more detail below.

Initiating the transaction may include referencing a local database 216 stored in the memory 210 or one or more of a remote transaction server 260 via a network 250. The database 216 or transaction server 260 may include a plurality of entries indexed according to the same type of plot descriptor template as is used to generate the plot descriptor 240. If multiple alternative plot descriptor templates are defined by the circular plot definition 214, the entries in the database 216 or transaction server 260 may be multiply indexed according to each of the alternative plot descriptor templates to support comparison with other circular plots on the basis of multiple alternative plot descriptors 240. For example, the circular plot definition 214 may define two plot descriptor templates for a strong plot descriptor and a weak plot descriptor, respectively. The strong plot descriptor may more precisely identify the circular plot 280 or contain more information but may require a processor 220 with more processing power or a circular plot 280 that is in better condition for image-based recognition (e.g. higher resolution, pristine condition without printing errors or damage to medium, etc.). The weak plot descriptor may less precisely identify the circular plot 280 or contain less information but not have as stringent requirements, a descriptor having less fidelity for example. If the entries in the database 216 or transaction server 260 are multiply indexed according to both the strong and the weak plot descriptor, the circular plot analysis agent may reference the database 216 or transaction server 260 using a weak plot descriptor 240 when it is not possible or convenient to generate a strong plot descriptor 240. Such an approach is advantageous when circumstances dictate that digital image 230 has less fidelity possibly due to distance between camera 270 and circular plot 280, focus, lighting conditions, or other environmental factors.

If the device 200 interfaces with the camera 270, the device 200 may instruct the camera 270 to capture additional digital images 230 on the basis of feedback from the various process performed by the plot analysis agent executed by the processor 220. For example, if a detected perimeter 231 is unable to be transformed as necessary (S293, see also FIG. 3), the plot analysis agent may cause the camera 270 to capture an additional digital image 230 and/or provide instructions to a user via a user interface regarding the need to capture another digital image 230.

In the example described above with respect to FIGS. 1, 2A, and 2B, a digital image 230 is captured by a camera 270 (e.g. a camera of a doctor's phone 125). However, image data of the circular plot 130 (e.g. image 230) may instead be transmitted device-to-device (e.g. patient's phone 115 to doctor's phone 125) by known methods of electronic transmission without any optical process. In this case, device-to-device communication may also include control and adjustment of settings of the circular plot 280 for presentation to the device 200 (doctor's phone 125). For example, only a portion of the circular plot 280 may be presented, with some data (e.g. one or more tracks) removed, hidden, or enhanced by cropping or zooming. Privacy of the patient may be maintained by any of various known means. In some embodiments, a short ranged wireless communication system can be employed that requires both devices to be intentionally placed proximal to each other. Example close proximity and high bandwidth wireless technology includes the 60 GHz (e.g., WiGIG, 802.11ad, etc.) offerings by Keyssa® (see URL www.keyssa.com) or by Tensorcom™ (see URL www.tensorcom.com).

Figure 3:
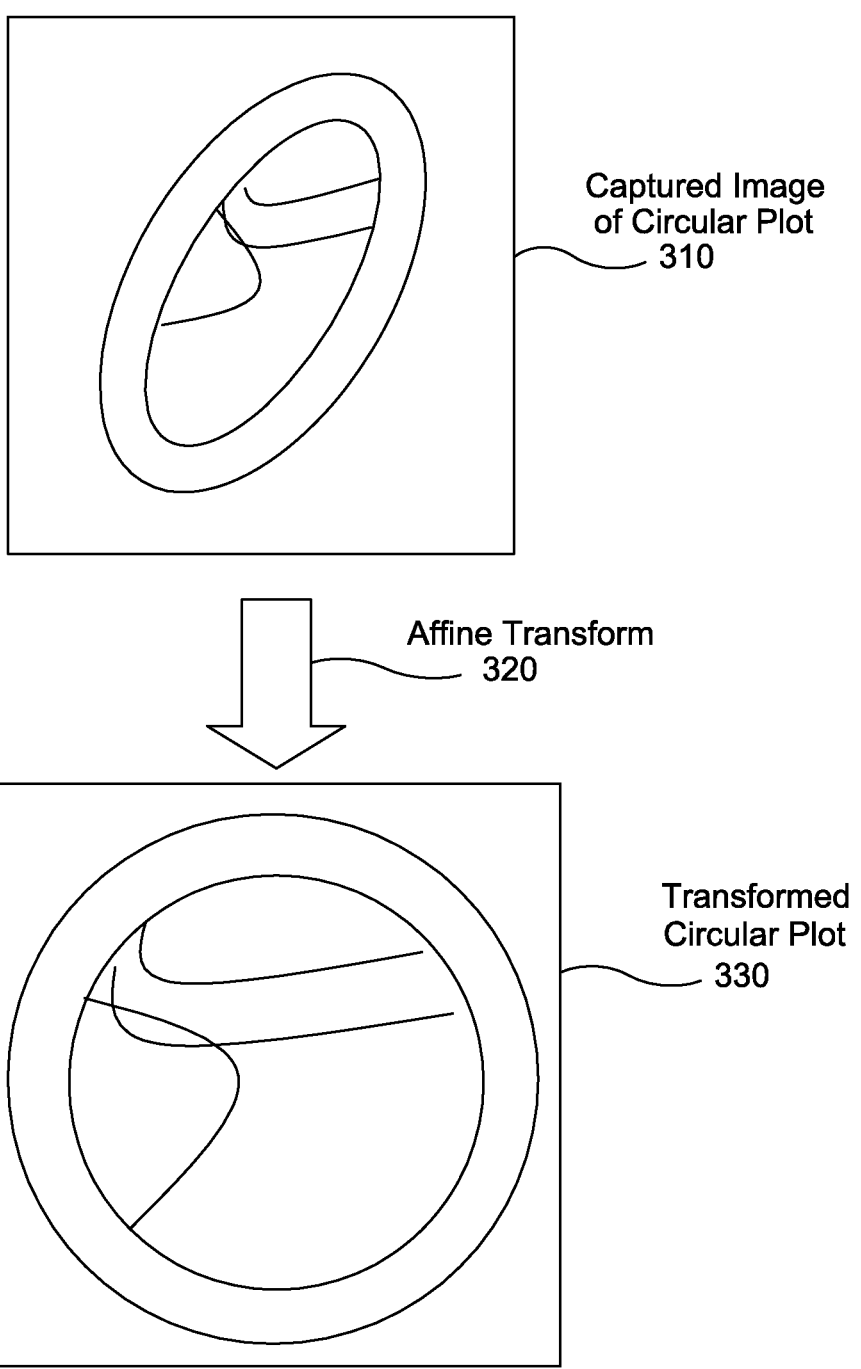
FIG. 3 illustrates an example of transforming a skewed captured image of a circular plot into a circularized plot via an affine transform.

FIG. 3 illustrates an example of transforming a skewed captured image 310 of a circular plot into a circularized plot 330 via an affine transform 320. When the circular plot 280 is captured by the camera 270, any slight difference in angle between the camera 270 and the circular plot 280 will result in the digital image 230 being a skewed captured image 310 as shown in FIG. 3, which is not truly circular but elliptical or some other shape. In order to greatly simplify the subsequent analysis, the circular plot analysis agent executed by the processor 220 may correct this skewing to produce a transformed digital image 330 of the circular plot for further analysis by the circular plot analysis agent. For example, the circular plot analysis agent may detect a perimeter 231 of the skewed captured image 310 using an edge detection algorithm based on Canny edges, edge descriptors, edge constellation descriptors or any other type of edge detection algorithm, though the perimeter 231 may not be circular. The circular plot analysis agent may then perform affine transform 320 to convert the skewed captured image 310 to a transformed digital image 330 in a coordinate system in which the detected perimeter 231 is circularized. The fitness of the transformed digital image 330 can be determined by comparing the perimeter edges of the plot to an actual circle. The comparison can be performed by measuring the deviation of the transformed image's perimeter's edge to an edge of a perfect circle. For example, the deviation (e.g., a distance from the perimeter edge to the perfect circle imposed on the transformed image, a square of the distance, etc.) can be measured at multiple points (e.g., 4 points, 8 points, pixel-by-pixel, etc.) around the perimeter and then summed together to calculate a fitness measure or circularity measure. The affine transform 320 can be iterated until the fitness measure or circularity measure is minimized. Many other transforms and corrections may be performed as well in addition to or instead of the affine transform 320. For example, the originally captured digital image 230 may be converted to grayscale, color corrected or adjusted, scaled, stretched, skewed, centered, cropped or clipped to remove background, etc. depending on the particular embodiment and, in some cases, as defined by the circular plot definition 214.

It is noted that multiple perimeters 231 may be detected by the circular plot analysis agent and that one (e.g. the outermost) may be selected for purposes of transforming the skewed captured image 310. Selection of a detected perimeter 231 may done by the circular plot analysis agent in accordance with the circular plot definition 214. Furthermore, detection of the perimeter(s) 231 may itself be done in accordance with the circular plot definition 214. For example, the circular plot definition 214 may inform the circular plot analysis agent that only a single perimeter is expected, allowing an edge detection algorithm to more strictly interpret candidate perimeters to find the most likely candidate (e.g. by adjusting a threshold). As another example, the circular plot definition 214 may inform the circular plot analysis agent that three perimeters 231 (e.g.

concentric tracks) are expected, requiring the edge detection algorithm to less strictly interpret candidate perimeters until three perimeters are found.

Figure 4:
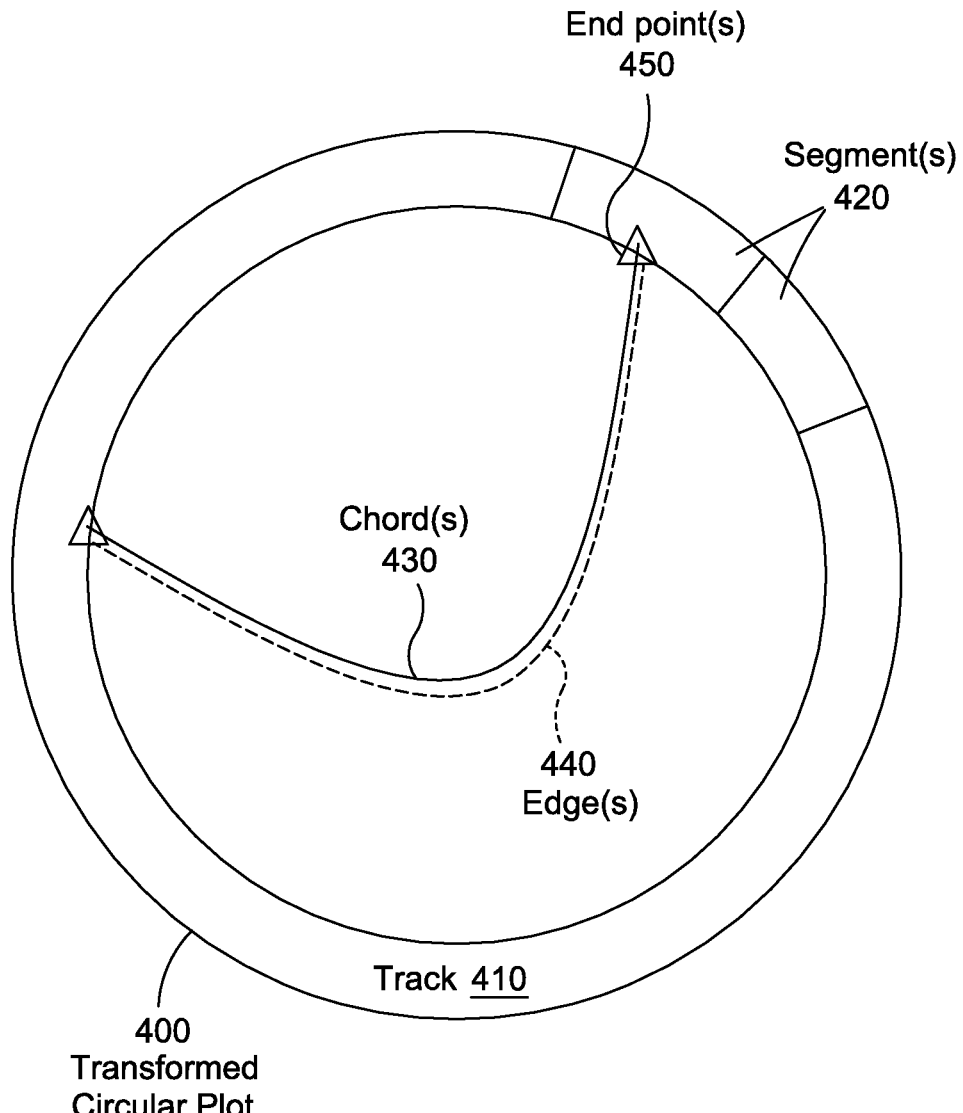
FIG. 4 illustrates an example of converting observed edges in a circular plot into observed chord endpoints FIG. 5 provides an example of converting observed endpoints into an orientation dependent descriptor.

FIG. 4 illustrates an example of converting observed edges 440 in a digital image 400 of a circular plot 280 into observed chord endpoints 450. As explained above, the circular plot analysis agent executed by the processor 220 may obtain a digital image 230 of a circular plot 280 and transform the digital image 230 (e.g. affine transform) for further analysis. The digital image 400 shown in FIG. 4 is an example of such a transformed digital image of a circular plot, including only a single chord 430 for the sake of discussion. As can be seen, the chord 430 extends between two endpoints 450 on the track 410. The endpoints 450 may be located in segments 420 (and in some cases at specific positions within segments 420). After the perimeter 231 has been detected (and possibly transformed), the circular plot analysis agent may detect a plurality of edges 233 within the perimeter 231 (e.g. the innermost perimeter if there are multiple, as may be defined by the circular plot definition 214) using an edge detection algorithm based on Canny edges, edge descriptors (see U.S. Pat. No. 9,412,176 to Song et al. titled "Image-Based Feature Detection Using Edge Vectors", filed May 6, 2015), edge constellation descriptors (see U.S. Pat. No. 9,665,606 to Song et al. titled "Edge-Based Recognition, Systems and Methods, filed Feb. 16, 2015), the content and substance of which is incorporated herein by reference, or any other type of edge detection algorithm. In the example of FIG. 4, a single edge 440 is detected within track 410 (the perimeter 231) corresponding to the single chord 430.

With the edge 440 having been detected, the circular plot analysis agent identifies a set of endpoints 235 on the perimeter 231 as a function of the detected edge 440. For example, the circular plot analysis agent may identify intersections or near intersections between the detected edge 440 and track 410 (the perimeter 231). In some embodiments, edges 440 can be represented by one or more curve primitives (e.g., circular arcs, parabolas, lines, hyperbolas, ellipsoidal arcs, etc.). Thus, it should be appreciated that the circular plot analysis agent, upon detecting the edges, may have the parameters of the edges and may therefore be able to project edges 440 to the perimeters of track 410. In the example of FIG. 4, a pair of endpoints 450 are identified. Segments 420 may be detected using an edge detection algorithm and/or determined based on the circular plot definition 214 as described below. If segments 420 have been detected by the circular plot analysis agent, the segment 420 corresponding to each endpoint 450 may be identified based on the position of the endpoint 450 on track 410.

Figure 5:
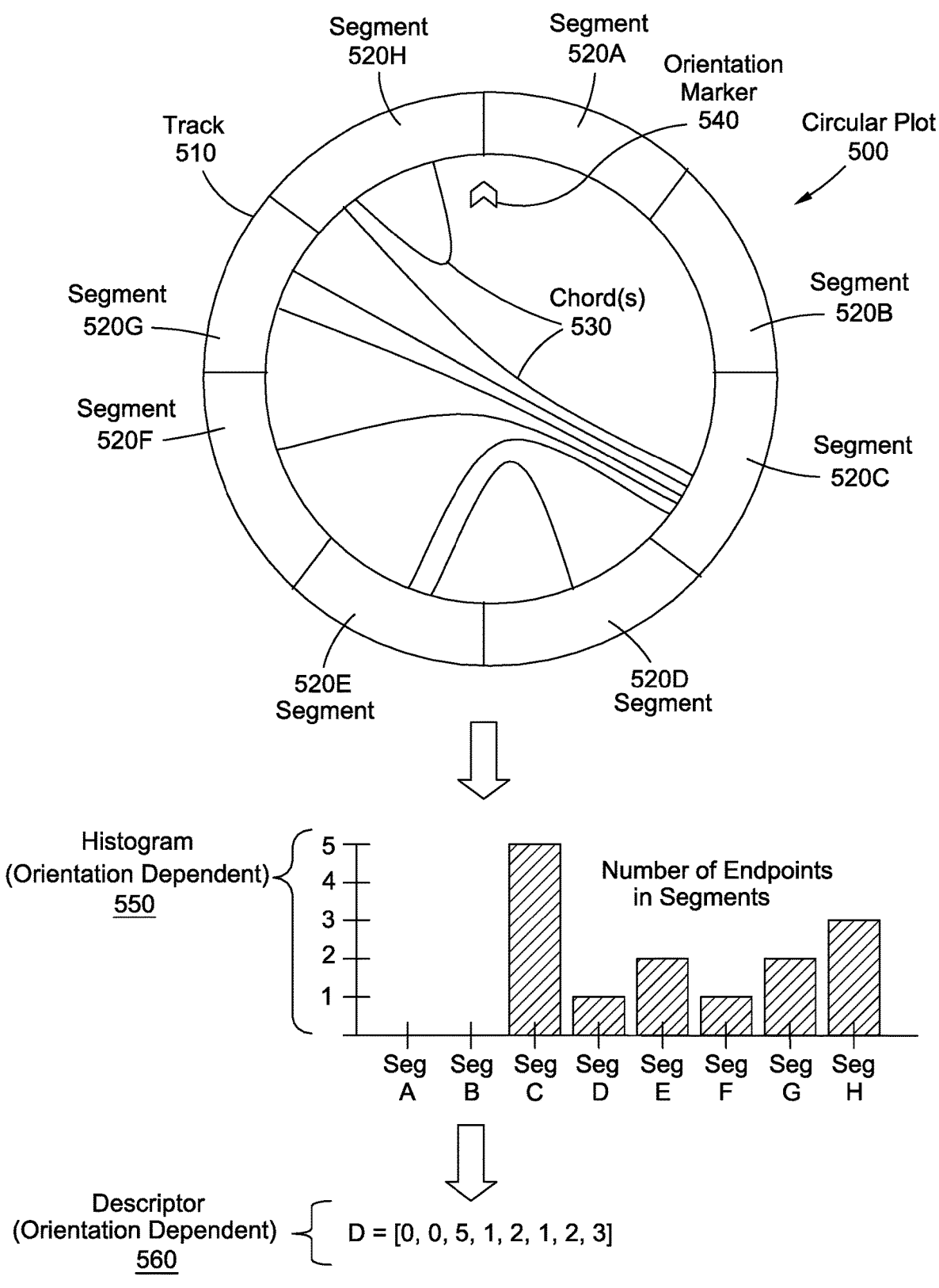

FIG. 5 provides an example of converting observed endpoints 235 into an orientation dependent descriptor 560. The circular plot 500 shown in FIG. 5 has a single track 510 and eight segments 520A-520H. The circular plot 500 also has an orientation marker 540 indicating the correct orientation for analysis by the circular plot analysis agent executed by the processor 220. When a digital image 230 of the circular plot 500 is obtained by the circular plot analysis agent, the circular plot analysis agent may consult the circular plot definition 214 stored in the memory 210 as described above. The circular plot definition 214 may inform the circular plot analysis agent that there is a single track 510 and an orientation marker 540 and may further define segments 520A-520H in relation to the orientation marker 540. On the basis of the circular plot definition 214, the circular plot analysis agent may detect the single perimeter 231 corresponding to track 510 as described above and may further detect the orientation marker 540 in the same way (e.g. by edge detection). Alternatively, the orientation marker 540 may not be detected by the circular plot analysis agent and may instead serve as an instruction to the user of the camera 270 to orient the circular plot 500 in a particular way when capturing the digital image 230 (e.g. with the orientation marker 540 at the top). In either case, the locations of segments 520A-520H may consequently be known by the circular plot analysis agent in accordance with the orientation marker 540 and circular plot definition 214. As another alternative, the segments 520A-520H may be detected (e.g. by edge detection), either assisted by presumed segment positions defined by the circular plot definition 214 as described above or without such assistance.

Having detected the perimeter 231 of the digital image 230 and with the known track 510 and segments 520A-520H having been detected or derived on the basis of the perimeter 231 (e.g. the perimeter 231 may be converted into a perimeter track defined by the circular plot definition 214 and including known segments, labels, etc.), the circular plot analysis agent proceeds with detecting a plurality of edges 233 within the perimeter 231, which may be understood to correspond to the chords 530 of the circular plot 500, and identifying a set of endpoints 235 on the perimeter 231 as a function of the plurality of edges 233. For example, the circular plot analysis agent may detect edges 233 using an edge detection algorithm as described above and may identify the endpoints 235 as the points of intersection or near intersection between the detected edges 233 and the detected perimeter 231. In a case where many edges 233 are clustered and overlapping near the perimeter 231 (see FIG. 7), an exact count of endpoints 235 may be impractical and the circular plot analysis agent may instead approximate or prorate the set of endpoints 235 using the thickness of overlapping endpoint regions or the number of incoming and outgoing edges 233 representing chords 530. In a case where chord thickness is variable (as defined by the circular plot definition 214), the set of endpoints 235 may further include ranges of values indicating the extent of each endpoint 235 on the perimeter 231 or within a given segment. This can be achieved, again, through projecting the detected edges associated with chords 530 to segments 520 based on the detected edges' curve primitives.

Using the detected endpoints 235 and the known segments 520A-520H (i.e. the known positions of segments 520A-520H on the track 510 corresponding to the detected perimeter 231), the circular plot analysis agent generates one or more plot descriptors 240 such as the descriptor 560 shown in FIG. 5. As shown in FIG. 5, the circular plot analysis agent may first generate a histogram 550 counting the number of endpoints 235 in each of a plurality of bins corresponding to the segments 520A-520H. In the histogram 550, for example, the counts in each bin are as follows: 520A=0, 520B=0, 520C=5, 520D=1, 520E=2, 520F=1, 520G=2, and 520H=3. From this, the descriptor 560 is defined as the set of histogram counts beginning with the first segment 520A and proceeding clockwise to the last segment 520H: D=[0, 0, 5, 1, 2, 1, 2, 3]. The first segment, last segment, and clockwise direction may be defined relative to the orientation marker 540 as defined by the circular plot definition 231.

In the example of FIG. 5, the descriptor 560 does not specify the detected endpoints 235 as being sources or destinations (i.e. sinks) of the chords 530. In some circular plots, directionality of chords 530 may be represented as a feature of the intersection of a chord 530 with a track 510.

For example, a source of a chord 530 may be represented as a touching of the chord 530 to the track 510 while a destination of a chord 530 may be represented as an abrupt ending of the chord 530 very near but not touching the track 510, or vice versa. If it is desirable for source and destination information to be included in a descriptor 240, this may be accomplished in various ways. For example, as endpoints 235 are identified, they may be recorded as sources or destinations in accordance with the details of how the detected edge 233 relates to the detected perimeter 231 (e.g. intersections interpreted as sources, near intersections interpreted as destinations). Then, when generating the descriptor 240, the histogram 550 may be modified to include a pair of bins for every segment 520A-520H, e.g. 520A$_{source}$, 520A$_{destination}$, 520B$_{source}$, 520B$_{destination}$, etc. with separate counts. The descriptor 560 may thus be modified accordingly.

It should be noted that, in the example of FIG. 5, the circular plot analysis agent need not determine the actual paths of the chords 530, relying only on the detected edges 233 and perimeter 231 to identify the endpoints 235 and thus generate the plot descriptor 240. However, in other examples, plot descriptors 240 may further include information about which endpoints 235 connect to each other, and thus knowledge of the actual paths of the chords 530 may be required. In such a case, the actual paths of chords 530 may be inferred from the detected edges 233 (e.g. the detected edges 233 may be converted into the chords 530), possibly based on curve primitives associated with the detected edges 233. In the example of FIG. 5, the chords 530 do not cross or overlap and thus the correspondence between edges 233 and chords 530 may be straightforward. In other cases, where the chords 530 cross or overlap, the edge detection algorithm may yield a plurality of edges 233 that is greater or less in number than the number of chords 530 and/or does not directly correspond to the chords 530, in which case the circular plot analysis agent may further infer the positions of chords 530 from the detected plurality of edges 233. For example, where two chords 530 intersect, the circular plot analysis agent may infer which portions of the detected edges emerging from the point of intersection belong to which chords 530 by approximating the shape of a chord 530 with a polynomial derived from one or more detected edges 233 and interpolating or extrapolating to presume which additional edges 233 belong to the chord 530. Then, when generating the descriptor 240, the histogram 550 may be modified to include a bin for every pair of segments 520A-520H (including identity pairs), e.g. 520AA, 520AB, 520AC, 520AD, 520AE, 520AF, 520AG, 520AH, 520BB, 520BC, 520BD, etc. with separate counts. The descriptor 560 may thus be modified accordingly. The histogram 550 and descriptor 560 may further include source/destination information, in which case there may further be separate bins for 520AB and 520BA, etc. In some embodiments, a matrix of endpoints can be constructed where one dimension of the matrix represents segments as sources and a second dimension represents segments as destinations. The cells of the matrix would then include a number of endpoints satisfying the source-destination pair from chords 530. A final descriptor can be generated from the matrix by projecting the counts along one or more axes. For example, the projection along both the source and destination axes would generate a source and a destination histogram. These two histograms can be concatenated to form a single descriptor. Naturally, more complex projections are also possible along other transformed axes, which would result in different, less trivial descriptors (projecting along a diagonal for example).

Figure 6:
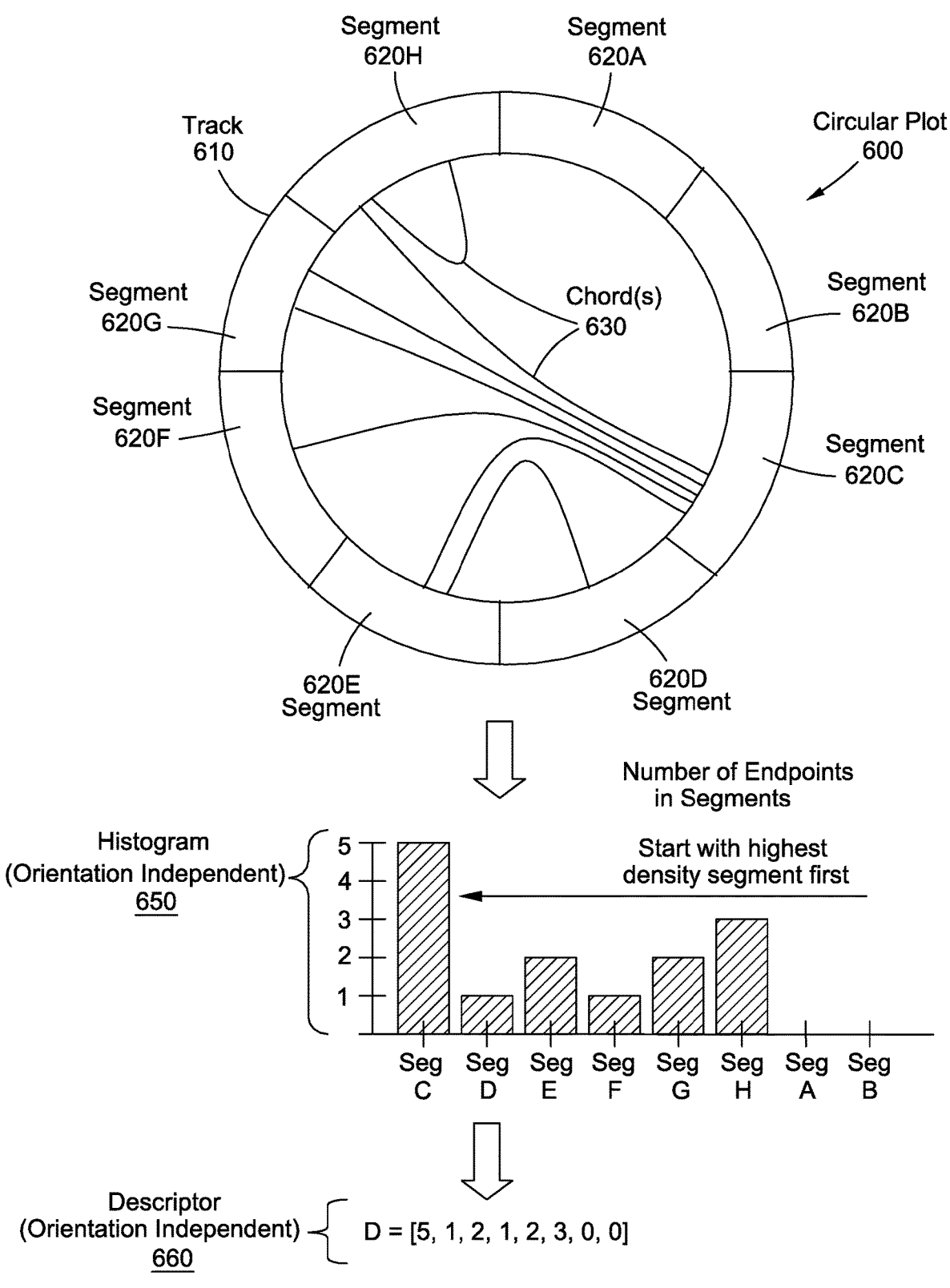
FIG. 6 provides an example of converting observed endpoints into an orientation independent descriptor.

FIG. 6 provides an example of converting observed endpoints 235 into an orientation independent descriptor 660. Like the circular plot 500 of FIG. 5, the circular plot 600 shown in FIG. 6 has a single track 610 and eight segments 620A-620H. However, unlike the circular plot 500, the circular plot 600 does not have an orientation marker and there is no specified orientation of the circular plot 600 for analysis. This may be by design or may be the result of the loss of a usable orientation mark due to a printing error or damage to the medium, in which case the orientation independent descriptor 660 may be an example of a weak plot descriptor whose template might coexist in the circular plot definition 231 with that of a strong plot descriptor like the descriptor 560. When a digital image 230 of the circular plot 600 is obtained by the circular plot analysis agent executed by the processor 220, the circular plot analysis agent may consult the circular plot definition 214 stored in the memory 210 as described above. The circular plot definition 214 may inform the circular plot analysis agent that there is a single track 610 and may define segments 620A-620H in relation to each other (e.g. number, order, size of each segment), though their positions on the track 610 may be unknown. On the basis of the circular plot definition 214, the circular plot analysis agent may detect the single perimeter 231 corresponding to track 610 as described above. In some cases, the segments 620A-620H may be detected (e.g. by edge detection), either assisted by presumed segment number, order, size defined by the circular plot definition 214 as described above or with no such segment definitions.

After detecting a plurality of edges 233 within the perimeter 231 and identifying a set of endpoints 235 on the perimeter 231 as a function of the plurality of edges 233 in the same way as described with respect to FIG. 5, the circular plot analysis agent generates one or more plot descriptors 240 such as the descriptor 660 shown in FIG. 6. As shown in FIG. 6, the circular plot analysis agent may first generate a histogram 650 counting the number of endpoints 235 in each of a plurality of bins corresponding to segments 620A-620H. If the positions of segments 620A-620H are known, e.g. with the help of edge detection, this may be done just like in the example of FIG. 5. If the positions of segments 620A-620H are unknown, the number and/or size of segments 620A-620H may still be known from the circular plot definition 214. In this case, the circular plot analysis agent may presume the position of a first segment according to some rule, e.g. based on a high density of endpoints. For example, the circular plot analysis agent may presume the position of a first segment to be the location of a centroid of the highest-density cluster of endpoints. Then, using the known number and/or size of segments 620A-620H, the circular plot analysis agent may presume the positions of the other segments.

In the example of FIG. 6, the positions of the segments 620A-620H are known (e.g. by edge detection), so the histogram 650 is generated in substantially the same way as in FIG. 5, but with one exception. Since there is no defined orientation for the circular plot 600, none of the segments 620A-620H is defined as being the first bin of the histogram 650 or descriptor 660 (which was determined in the case of the circular plot 500 based on the orientation marker 540). Therefore, the circular plot analysis agent selects one of the segments 620A-620H according to the circular plot definition 214, e.g. according to a rule that the segment containing the most endpoints 235 should be designated as the first segment. Thus, segment 620C is selected as the first segment and defines the first bin of the histogram 650, with the remaining segments in clockwise order defining the remaining bins as follows: 620C=5, 620D=1, 620E=2, 620F=1, 620G=2, 620H=3, 620A=0, and 620B=0. From this, the descriptor 660 is defined as the set of histogram counts beginning with the selected first segment 620C and proceeding clockwise to the last segment 620B: D=[5, 1, 2, 1, 2, 3, 0, 0].

If the positions of the segments were unknown and presumed, the descriptor 660 could be generated in the same way using the presumed segments. While such an arbitrary descriptor would represent a distorted picture of the original data that produced the circular plot 600, it may still be used to generate a transaction as described herein as long as the contents of the database 216 or transaction server 260 are indexed by the identically defined arbitrary descriptor. For example, if the database 216 or transaction server 260 contains circular plot descriptors generated based on presumed segments using the rule that there are six equal-sized segments proceeding clockwise from the centroid of the highest-density cluster of endpoints, the plot analysis agent may initiate a transaction with the database 216 or transaction server 260 using a descriptor generated according to the same rule. Even though the values of the descriptor may have no meaningful relationship with the original data, they can still be used for matching with other data that has been indexed according to the same schema.

Figure 7:
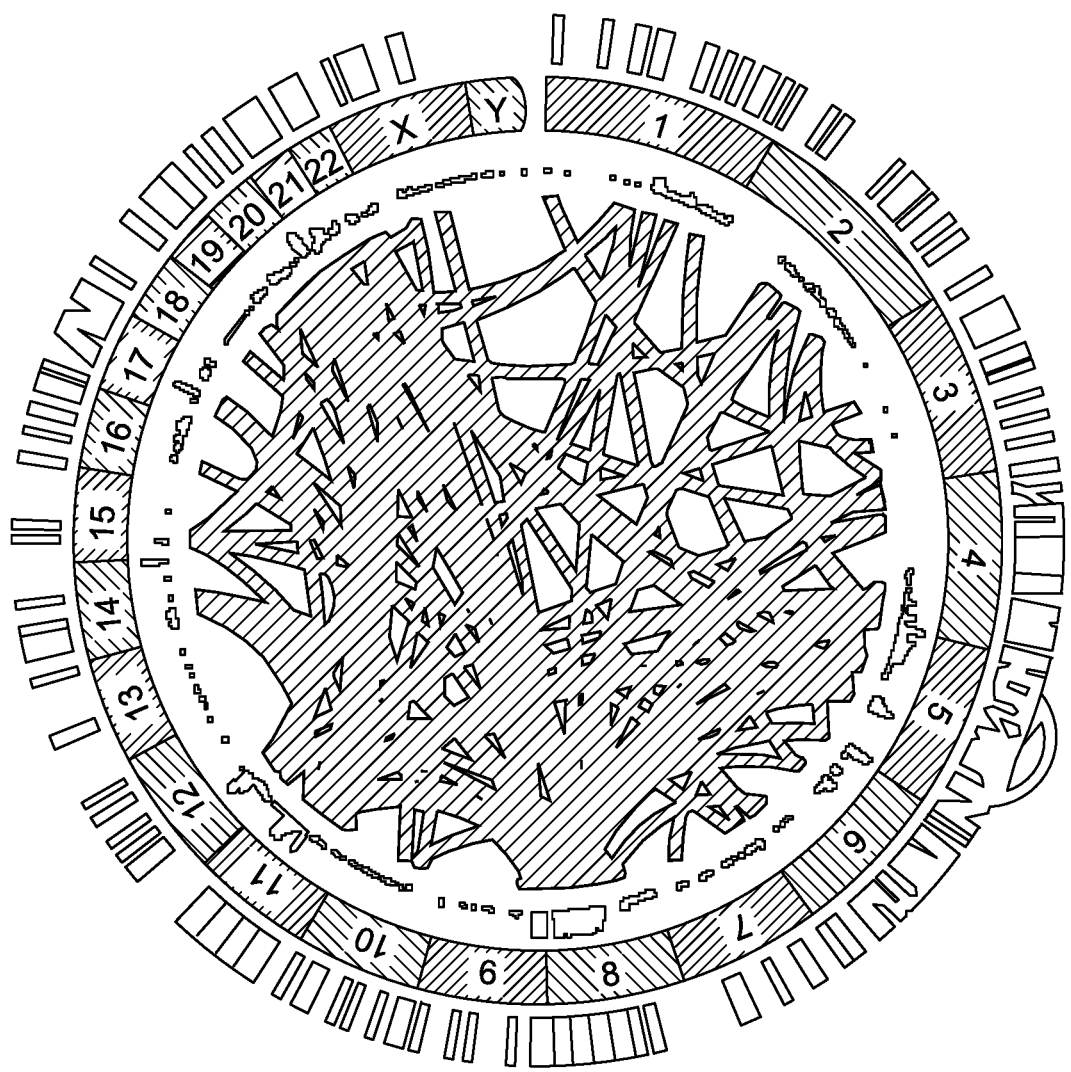
FIG. 7 represents an example whole genome sequence circular plot of a patient's tumor.

FIG. 7 represents an example whole genome sequence circular plot of a patient's tumor. In the example shown in FIG. 7, the numbered tracks 1-22, X, Y represent chromosomes and the chords represent chromosomal rearrangements. As explained above, a doctor viewing the circular plot of FIG. 7 may be able to make some determinations about the patient through visual observation. For example, the high number of chords may indicate that the patient's condition is severe. If the doctor has access to additional circular plots representing earlier test results of the same patient, the approximate rate of increase in the number of chords may provide some indication of how rapidly the patient's condition is worsening. However, beyond these basic observations, it may be difficult for the doctor to learn more from the circular plot. The doctor might visually observe that there is a high density of chords between particular chromosomes, but since every cancer is different, it may be hard for the doctor to draw conclusions from this observation. Moreover, even if the doctor could draw conclusions from the details of circular plot, the low resolution of the image may make it difficult to discern the details.

The innovations described herein and shown in the drawings provide healthcare providers additional tools by which the doctor can interpret circular plots like that of FIG. 7 to assist with the counseling, diagnosis, and treatment of the patient. In particular, whereas a complete understanding of the underlying data of a patient circular plot may be impossible for doctor and computer alike (considering the resolution, volume of data, etc.), the innovative descriptors described herein provide a useful basis for searching, comparison, etc. of the patient circular plot against other stored circular plots, despite the patient circular plot being generated from incomplete, fuzzy, or even incorrect or arbitrary image recognition data of such plot. For example, the circular plot analysis agent executed by the processor 220 may generate a plot descriptor for the circular plot of FIG. 7 similar to the plot descriptor 550 of FIG. 5. (As noted above, an approximate count of endpoints in each histogram bin representing sections/chromosomes may be used instead of an exact count if necessary.) The descriptor may define endpoint counts from chromosome 1 through chromosome Y, like this (with the: D=[6, 6, 5, 12, 12, 8, 3, 30, 4, 3, 20, 9, 0, 3, 4, 1, 4, 1, 10, 12, 8, 6, 2, 0]. The descriptor D may then be compared to identically or similarly constructed descriptors representing other circular plots stored in the database 216 or transaction server 260, possibly using a K-nearest neighbor search based on one or more tree data structures. The comparison may yield useful medical information about a patient's circular plot by potentially categorizing it with like stored plots that have known medical data attached to such plots. In one example, it may be determined that the analyzed patient circular plot, could be categorized within a group of stored circular plots that have responded favorably to a particular pharmaceutical drug. In this regard, it could be deduced by the healthcare provider that a particular patient from which the patient circular plot was derived, is a good candidate for a particular drug treatment. Comparison may be performed by any known method or definition of similarity, e.g. Euclidean distance, Hamming distance, kNN algorithm, etc. The circular plot analysis agent, may initiate a transaction including comparison of the plot descriptor of the patient's plot to those of other circular plots that are stored in the database 216 or transaction server 260 in relation to diagnoses, patient outcomes, drug efficacies, drug interactions, resistances, ongoing/upcoming clinical trials, insurance programs, etc. The output of the transaction may be a presumed diagnosis, a recommended prescription, a prognosis, a warning, a resistance factor, a transaction key, or any other information usable by the doctor with respect to the patient. In some cases, the output of the transaction might be a notification that the patient may be a candidate to participate in a clinical trial involving other patients with similar tumors.

It should be noted that the plot descriptor of the patient's circular plot may contain readily interpretable information of the underlying data of the patient's circular plot. In this sense, the plot descriptor may be a hybrid between a complete reading (like a bar code) and a conventional object recognition descriptor (e.g. a SIFT descriptor). For example, in the case of D=[6, 6, 5, 12, 12, 8, 3, 30, 4, 3, 20, 9, 0, 3, 4, 1, 4, 1, 10, 12, 8, 6, 2, 0], there are particularly high counts of 30 and 20 corresponding to the patient's eighth and eleventh chromosomes and zero counts corresponding to the patient's thirteenth and Y chromosomes. Even in a case where positions of sections (i.e. chromosomes) are not know and must be presumed, such information may still remain. For example, a very high count, even if incorrectly divided between two adjacent bins, may still be relatively high. Additional information of this sort may be used in various ways. For example, the process of comparing the descriptor to entries in the database 216 or transaction server 260 may be quicker, more efficient, more accurate, and/or require reduced processing load and/or memory if a tree (e.g. a binary tree) is navigated to reduce the number of comparisons that need to be made. Counts above or below thresholds in particular chromosomes may, for example, narrow down the range of possible matches as the search algorithm traverses the tree (e.g. if Y=0, the algorithm may ignore some segment of the database). As another example, the additional information inherent in the plot descriptor may be used directly to produce transaction output in accordance with predefined rules. For instance, a count above a threshold in a particular chromosome or group of chromosomes might bypass the search entirely or supplement the search with a presumed diagnosis, recommended prescription, etc.

based on a rule devised on the basis of evidence-based medicine or other accumulated knowledge.

In another instance, the circular plot analysis agent might limit the scope of a search or use a smaller database or subset of the database 216 or transaction server 260, for example, to compare the descriptor D of the patient's circular plot with only the patient's own past circular plots. Instead of a match/similarity, the transaction may involve comparing the descriptor D with descriptors of past circular plots associated with the same tumor (or healthy tissue) to discern a rate of change with respect to time. Output may include a numerical or graphical representation of various trends, e.g. trends in the total number of chromosomal rearrangements, trends in the number of chromosomal rearrangements of specific chromosomes, etc. as well as conclusions based on such trends (e.g. a presumed diagnosis, recommended prescription, likely outcome, etc.) The circular plot analysis agent may approximate trends using polynomials and determine rates of change by taking higher order derivatives of the polynomials, with respect to time or other factors for example.

In another instance, the circular plot analysis agent may be used to identify the patient. For example, when comparing the descriptor D of the patient's circular plot to other plots in the database 216 or transaction sever 260, a similarity above a threshold may indicate a high likelihood that the patient's circular plot is the same as one of the circular plots in the database 216 or transaction server 260 or is a related circular plot of the same genomic data (e.g. the same tumor, healthy tissue, liquid biopsy, blood samples, etc.) taken at a different time or under different conditions. In such cases, an output of the transaction may include an identification or validation of the patient. Thus, the circular plot may be used as an ID for the patient, e.g. a temporary ID related to a current medical condition. A transaction identifying the patient may further include retrieving medical records, insurance records, etc. associated with the identified patient and may include checking if a particular drug or service is covered by the patient's insurance.

In general, the transactions that the circular plot analysis agent may perform using the plot descriptor are diverse and may include, for example, financial transactions including purchases (e.g. purchases of drugs, tests, or other services), database queries, prescriptions, diagnoses, prognoses, and other healthcare transactions, insurance transactions, notifications and alerts, event logging, cryptographic transactions, blockchain transactions, security transactions, etc. For example, the descriptor and/or the plot itself can be integrated into a patient's electronic medical records stored in the form of a blockchain (see U.S. Patent Application Publication 2015/0332283 to Witchey titled "Healthcare Transaction Validation via Blockchain Proof-of-Work, Systems and Methods," published Nov. 19, 2015, the content and substance of which is incorporated herein by reference). Further, the descriptor could operate as a cryptographic key to lock or unlock additional content.

In some cases, the circular plot 280 may be in color. The plot analysis agent executed by the processor 220 may therefore perform the various edge detections described throughout this disclosure in multiple color channels (e.g. HSV or RGB channels) and the circular plot definition 214 may define aspects of the circular plot 280 with reference to color. For example, chords of different colors may have different meanings that may be used by the plot analysis agent 220 in generating the descriptor(s) 240, such as a color code for classifying endpoints as sources or destinations. The descriptor(s) 240 themselves may also be hue-based, including color information of the chords connecting the endpoints represented by the descriptor for example.

As noted above, the memory 210 may include one or more circular plot definitions 214. If the device 200 supports multiple circular plot definitions 214, a plot type ID stored with each circular plot definition 214 may be used to distinguish between circular plot definitions 214. A user (e.g. a doctor) may then select between the circular plot definitions 214 using a user interface depending on what type of circular plot 280 is to be analyzed. Alternatively, or additionally, circular plots 280 may include bar codes or other identifying marks (e.g. on the outside of the circular plot 280), which may then be read by the camera 270 or other input device to inform the plot analysis agent which circular plot definition 214 to select for the circular plot 280.

The specific plot descriptors described throughout this disclosure are only examples. Other descriptors developed in accordance with the principles of the innovations described herein may be equally suitable or more or less suitable depending on the particular type of circular plot and the particular type of transaction initiated by the plot analysis agent. In this regard, descriptors may be modified or newly created depending on which features of the circular plot (endpoints, source/destination, non-chord features of additional tracks, color relationships, chord thickness, etc.) are most useful for each transaction, for example, by principle component analysis, which may be performed outside or within the device 200 (e.g. by the plot analysis agent executed by the processor 220). It should also be noted that descriptors need not be specific to a particular type of circular plot but may instead be specific to a class of circular plots, e.g. all circular plots having a specific number of tracks or all circular plots having a particular number of endpoints or endpoints per arc, segment, etc. Thus descriptors may be plot-level invariant, track-level invariant, track segment-level invariant, etc. Descriptors may be invariant to scale or may vary depending on the zoom level of a circular plot.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:

1. A device comprising:
a non-transitory, computer readable memory storing software instructions and at least one plot definition;
at least one processor coupled with the memory wherein the at least one processor is caused, by execution of the software instructions, to perform operations comprising:
obtaining a digital image of a representation comprising medical data of a patient, the representation including a plot of the medical data that is not representative of an object;

detecting a region of the plot within the digital image;

detecting a plurality of features from the region;

converting the plurality of features into structured data as a function of the plurality of features and according to the at least one plot definition;

associating a descriptor with one or more of the plurality of features and the structured data; and initiating a transaction involving at least the processor based on the descriptor, the transaction including a comparison of the representation to other representations associated with other patients.

2. The device of claim 1, wherein the plot includes one or more perimeter tracks, and the at least one plot definition includes a perimeter track definition.

3. The device of claim 2, wherein the perimeter track definition specifies how many perimeter tracks are included in the plot.

4. The device of claim 2, wherein the perimeter track definition specifies a meaning of each perimeter track.

5. The device of claim 2, wherein the perimeter track definition specifies a location of each perimeter track.

6. The device of claim 2, wherein at least one of the one or more perimeter tracks includes one or more track segments, and the at least one plot definition includes a track segment definition.

7. The device of claim 6, wherein the track segment definition specifies how many track segments are included in the at least one perimeter track.

8. The device of claim 6, wherein the track segment definition specifies a meaning of each track segment.

9. The device of claim 6, wherein the track segment definition specifies a location of each track segment.

10. The device of claim 1, wherein the at least one plot definition specifies an orientation of the plot.

11. The device of claim 1, wherein the transaction includes an alert.

12. The device of claim 1, wherein the descriptor comprises a histogram compiled from the structured data.

13. The device of claim 1, wherein the descriptor is a representation-level invariant descriptor.

14. The device of claim 1, wherein the descriptor is a region-level invariant descriptor.

15. The device of claim 1, wherein the descriptor is a feature-level invariant descriptor.

16. The device of claim 1, wherein the descriptor comprises a time-varying descriptor.

17. The device of claim 1, wherein the transaction involves communicating with a networked database server.

18. The device of claim 1, wherein the transaction involves communicating with a second device selected from the group consisting of: a cell phone, an electronic healthcare card, a smart watch, a fitness band, and a vehicle.

19. A non-transitory, computer readable medium storing at least one plot definition and software instructions that cause a processor to perform operations comprising:

obtaining a digital image of a representation comprising medical data of a patient, the representation including a plot of the medical data that is not representative of an object;

detecting a region of the plot within the digital image;

detecting a plurality of features from the region;

converting the plurality of features into structured data as a function of the plurality of features and according to the at least one plot definition;

associating a descriptor with one or more of the plurality of features and the structured data; and initiating a transaction involving at least the processor based on the descriptor, the transaction including a comparison of the representation to other representations associated with other patients.

20. A method comprising:

obtaining a digital image of a representation comprising medical data of a patient, the representation including a plot of the medical data that is not representative of an object;

detecting a region of the plot within the digital image;

detecting a plurality of features from the region;

converting the plurality of features into structured data as a function of the plurality of features and according to at least one plot definition;

associating a descriptor with one or more of the plurality of features and the structured data; and initiating a transaction involving at least the processor based on the descriptor, the transaction including a comparison of the representation to other representations associated with other patients.

\* \* \* \* \*